(12) United States Patent
Nilsson et al.

(10) Patent No.: US 12,702,737 B2
(45) Date of Patent: Aug. 11, 2026

(54) DIALYSIS SYSTEM HAVING ENHANCED FEATURES INCLUDING DRIP PREVENTION

(71) Applicants: VANTIVE US HEALTHCARE LLC, Deerfield, IL (US); VANTIVE HEALTH GMBH, Glattpark (CH)

(72) Inventors: Roger Nilsson, Hoor (SE); Bjorn Ericson, Lund (SE); Mats Nilsson, Veberod (SE); Henrik Hall, Lund (SE); Oskar Erik Frode Styrbjorn Fallman, Lund (SE)

(73) Assignees: Vantive US Healthcare LLC, Deerfield, IL (US); Vantive Health GMBH, Glattpark (CH)

( * ) Notice: Subject to any disclaimer, the term of this patent is extended or adjusted under 35 U.S.C. 154(b) by 143 days.

(21) Appl. No.: 18/215,528

(22) Filed: Jun. 28, 2023

(65) Prior Publication Data

US 2023/0414850 A1 Dec. 28, 2023

Related U.S. Application Data

(60) Provisional application No. 63/356,394, filed on Jun. 28, 2022.

(51) Int. Cl.

| | |
|---|---|
| ***A61M 39/22*** | (2006.01) |
| ***A61M 1/14*** | (2006.01) |
| ***A61M 1/16*** | (2006.01) |
| ***A61M 1/28*** | (2006.01) |

(52) U.S. Cl.

CPC ............ *A61M 1/281* (2014.02); *A61M 1/155* (2022.05); *A61M 1/159* (2022.05); *A61M 1/1672* (2014.02); *A61M 1/1686* (2013.01); *A61M 1/1688* (2014.02); *A61M 1/28* (2013.01); *A61M 1/282* (2014.02); *A61M 1/285* (2013.01); *A61M 39/22* (2013.01); *A61M 2205/15* (2013.01); *A61M 2205/273* (2013.01);

(Continued)

(58) Field of Classification Search

CPC .... A61M 1/155; A61M 1/159; A61M 1/1672; A61M 1/1686; A61M 1/1688; A61M 1/28; A61M 1/281; A61M 1/282; A61M 1/285; A61M 39/22; A61M 2205/15; A61M 2205/273; A61M 2205/3331; A61M 2205/502; A61M 2205/581; A61M 2205/583

See application file for complete search history.

(56) References Cited

U.S. PATENT DOCUMENTS

2011/0303597 A2* 12/2011 Gunther .............. A61M 1/1561 210/188

* cited by examiner

*Primary Examiner* — John Kim

(74) *Attorney, Agent, or Firm* — K&L Gates LLP

(57) ABSTRACT

A peritoneal dialysis ("PD") system includes a housing, a PD fluid pump housed by the housing, and a reusable patient line extending from the housing. The reusable patient line includes a distal end configured to be connected to a patient line connector provided by the housing. The PD system also includes at least one reusable PD fluid line extending from the housing, the at least one reusable PD fluid line including a distal end configured to be connected to a PD fluid line connector provided by the housing. The PD system further includes a control unit configured to cause the PD fluid pump to apply a negative pressure to at least one of the reusable patient line or the at least one reusable PD fluid line when connected, respectively, to the patient line connector or the PD fluid line connector.

20 Claims, 5 Drawing Sheets

(52) U.S. Cl.
CPC ............... *A61M 2205/3331* (2013.01); *A61M 2205/502* (2013.01); *A61M 2205/581* (2013.01); *A61M 2205/583* (2013.01)

DIALYSIS SYSTEM HAVING ENHANCED FEATURES INCLUDING DRIP PREVENTION

PRIORITY CLAIM

This application claims priority to and the benefit as a non-provisional application of U.S. Provisional Patent Application No. 63/356,394, filed on Jun. 28, 2022, the entire contents of which are hereby incorporated by reference and relied upon.

TECHNICAL FIELD

The present disclosure relates generally to medical fluid treatments, and in particular to dialysis fluid treatments that require fluid heating.

BACKGROUND

Due to various causes, a person's renal system can fail. Renal failure produces several physiological derangements. For instance, it is no longer possible to balance water and minerals or to excrete daily metabolic load. Additionally, toxic end products of metabolism, such as urea, creatinine, uric acid, and others, may accumulate in a patient's blood and tissue.

Reduced kidney function and, above all, kidney failure is treated with dialysis. Dialysis removes waste, toxins, and excess water from the body that normal functioning kidneys would otherwise remove. Dialysis treatment for the replacement of kidney functions is critical to many people because the treatment is lifesaving.

One type of kidney failure therapy is Hemodialysis ("HD"), which in general uses diffusion to remove waste products from a patient's blood. A diffusive gradient occurs across a semi-permeable dialyzer between the blood and an electrolyte solution, called dialysate or dialysis fluid, to cause diffusion.

Hemofiltration ("HF") is an alternative renal replacement therapy that relies on a convective transport of toxins from a patient's blood. HF is accomplished by adding substitution or replacement fluid to an extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins, and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins, and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis, and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, where the transfer of waste, toxins, and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. Automated PD machines, however, perform the cycles automatically, typically while the patient sleeps. The PD machines free patients from having to manually perform the treatment cycles and from having to transport supplies during the day. The PD machines connect fluidly to an implanted catheter, to a source or bag of fresh dialysis fluid and to a fluid drain. The PD machines pump fresh dialysis fluid from a dialysis fluid source, through the catheter and into the patient's peritoneal chamber. The PD machines also allow for the dialysis fluid to dwell within the chamber and for the transfer of waste, toxins, and excess water to take place. The source may include multiple liters of dialysis fluid including several solution bags.

The PD machines pump used or spent dialysate from the patient's peritoneal cavity, though the catheter, to drain. As with the manual process, several drain, fill, and dwell cycles occur during dialysis. A "last fill" may occur at the end of an APD treatment. The last fill fluid may remain in the peritoneal chamber of the patient until the start of the next treatment, or may be manually emptied at some point during the day.

Any of the above modalities using presterilized (e.g., bagged, dialysis fluid) run the risk of drips forming when fluidly connecting the bags for treatment. Another issue with presterilized bagged, dialysis fluid is that the bags may have residual or remaining PD fluid after treatment, which the patient or caregiver has to transport and discard or wait after treatment for the residual or remaining PD fluid to be delivered to a drain. A further problem with PD treatments is that sometimes the patient disconnects the patient's transfer set from the patient line, e.g., during a patient dwell, so that the patient can move to another room and perform a task. If the patient does not somehow inform the PD machine that the patient is disconnected from the patient line and the patient dwell ends, the PD machine will attempt to drain the missing patient, which creates issues including pulling air into the fluid circuit and creating drain volume inaccuracy.

An improved dialysis system, such as a PD system, addressing any one or more or all of the above problems is accordingly needed.

SUMMARY

The present disclosure sets forth an automated peritoneal dialysis ("PD") system, which provides one or more PD treatment improvement. The system includes a PD machine or cycler. The PD machine is capable of delivering fresh, heated PD fluid to the patient at, for example, 14 kPa (2.0 psig) or higher. The PD machine is capable of removing used PD fluid or effluent from the patient at, for example, between −5 kPa (−0.73 psig) and −15 kPa (−2.2 psig), such as −9 kPa (−1.3 psig) or higher. Fresh PD fluid may be delivered via a dual lumen patient line to the patient and is first heated to a body fluid temperature, e.g., 37° C. The heated PD fluid is then pumped through a fresh PD fluid lumen of the dual lumen patient line to a disposable filter set, which is connected to the patient's transfer set, which is in turn connected to an indwelling catheter leading into the patient's peritoneal cavity. The disposable filter set communicates fluidly with the fresh and used PD fluid lumens of the dual lumen patient line. The disposable filter set is provided in one embodiment as a last chance filter for the PD machine, which may be heat disinfected between treatments.

The system may include one or more PD fluid container or bag that supplies fresh PD fluid to the PD machine or cycler. The PD machine or cycler may include internal lines having two-way or three-way valves and at least one PD fluid pump for pumping fresh PD fluid from the one or more PD fluid container or bag to a patient and for removing used PD fluid from the patient to a house drain or drain container. One or more flexible PD fluid line leads from the PD machine or cycler's internal lines to the one or more PD fluid container or bag. The flexible dual lumen patient line mentioned above leads from the PD machine or cycler's internal lines to the patient. A flexible drain line leads from the PD machine or cycler's internal lines to the house drain or drain container. The system in one embodiment disinfects all internal lines, the PD fluid lines and the dual lumen patient line after treatment for reuse in the next treatment. The disinfection may involve heat disinfection using leftover fresh PD fluid.

It is contemplated in one embodiment to leave the disinfection fluid within the PD machine or cycler until the next treatment. The flexible PD fluid lines and the dual lumen patient line are accordingly wet upon disconnection from the PD machine or cycler. When, at the start of a new treatment, the patient or caregiver removes the PD fluid lines and the patient line from their docking connectors at the PD machine, there is a risk that fluid may leak from the distal ends of the lines before a reconnection to (i) new PD fluid containers or bags for the PD fluid lines and (ii) a new disposable filter set for the patient line.

To prevent dripping or leaking, the control unit of the PD machine or cycler is configured in one embodiment to open the appropriate valves and cause the PD fluid pump to apply negative pressure to the PD fluid lines and the dual lumen patient line prior to the patient or caregiver removing any of those lines during treatment setup. The negative pressure causes the flexible lines under negative pressure to collapse slightly. In this way, when the patient or caregiver removes those lines for treatment setup, the flexible fluid lines expand, causing a small amount of air to be sucked into the ends of the lines, preventing spillage or dripping.

Regarding the dual lumen patient line, it is contemplated to program the control unit to place either or both of the fresh and used lumens under negative pressure by opening at least one valve and running the PD fluid pump. When the negative pressure reaches a desired or set negative pressure, e.g., between −5 kPa (−0.73 psig) and −15 kPa (−2.2 psig), such as −9 kPa (−1.3 psig), the control unit causes at least one valve to close and the PD fluid pump to stop. The closure of the at least one fresh PD fluid valve locks the applied negative pressure in the fresh and/or used PD fluid of dual lumen patient line (assuming no leaks). The locked negative pressure awaits the patient or caregiver removal of the patient line from the PD machine or cycler during treatment setup. The same procedure is performed for each of the PD fluid lines, e.g., using the same PD fluid pump but opening and closing different valves specific to the PD fluid lines.

It is contemplated for the control unit during treatment setup to cause the user interface to audibly, visually, or audiovisually (i) prompt the patient to wait to remove any of the patient line and PD fluid lines until the system is ready (until the flexible lines are placed under negative pressure) and/or (ii) prompt the patient that the system is ready for any of the patient line and PD fluid lines to be removed for treatment setup (e.g., the flexible lines have been placed under negative pressure). In this manner, the patient or caregiver is guided so that setup is performed in a manner that tends to prevent spillage and drips.

The negative pressures just described enable the flexible lines to be connected to the PD machine or cycler in a horizontal manner. The patient or caregiver may then initially pull the flexible lines horizontally off of their respective connectors and then tilt distal ends of the flexible lines vertically upward so that the disinfection fluid is cupped within the distal ends. The removal of the flexible lines under negative pressure causes the lines to expand and to pull air into the distal ends, preventing spillage during the time that the patient or caregiver removes the distal ends and tilts them upwardly. The distal ends may then be connected and sealed to new PD fluid containers or bags (PD fluid lines) and a new disposable filter set (patient line), respectively, without any spillage or dripping of the disinfection fluid, e.g., PD fluid.

A second PD treatment improvement feature of the present disclosure, which may be provided alternatively or in addition to the drip prevention feature, involves a PD fluid container or bag emptying feature, which helps to reduce the weight and mess associated with the removal and discarding of disposable items after treatment. It is possible, and in many instances likely, that residual or leftover PD fluid remains within one, or more, or all of the PD fluid containers or bags at the end of treatment. The volume of a patient fill for a PD treatment is determined typically via a patient's prescription, which sets a volume of fresh PD fluid to be delivered to the patient for each patient fill. The volume of the patient fill, e.g., 1.5 to two liters, is typically less than the volume of the PD fluid container or bag, e.g., two liters. Based on these volumes, there tends to be some fresh PD fluid leftover in the container or bag. Normally, the patient or caregiver either has to wait after treatment while the residual PD fluid is drained or has to forgo draining and transport the bags with the remaining fluid for disposal. The residual fluid adds weight and potential spillage and mess to the bag disposal.

To help mitigate the problems associated with leftover fluid after treatment, the control unit of the PD machine or cycler of the present disclosure is configured in one embodiment to remove residual PD fluid from the PD fluid containers or bags during one or more patient dwell. During a patient dwell a PD cycler is typically inactive. The PD machine or cycler of the present disclosure, on the other hand, makes use of the ample time provided during one or more patient dwell, to drain the PD fluid containers or bags (to house drain or drain container) so that they are empty, or as empty as possible, at the end of treatment. In this way, the patient or caregiver may more easily dispose the PD fluid containers, which are lighter and cleaner than if the bags contained residual PD fluid. But here, the patient does not have to wait after treatment and can dispose of the PD fluid containers or bags immediately after the end of treatment.

In one embodiment, the control unit waits for the final patient dwell to remove any residual PD fluid from any of PD fluid containers or bags. During the final patient dwell, the control unit causes appropriate valves to be opened or toggled at different times to pull residual PD fluid from a desired PD fluid container or bag via the PD fluid pump. During each of the different bag draining sequences, the control unit also causes one or more drain valve to be opened so that the PD fluid pump may pump residual PD fluid from one of the PD fluid containers or bags to drain. In an alternative embodiment, the control unit uses each patient dwell of a treatment, or at least one intermediate patient dwell to remove any residual PD fluid from the most recently used PD fluid container or bag.

It is also possible that any one or more of the PD fluid containers or bags contains more than one patient fill volume's worth of fresh PD fluid. The control unit in one embodiment knows the volume of each the PD fluid containers or bags and is configured to wait until the patient dwell occurring after the PD fluid container or bag has been almost fully emptied before attempting to fully drain any residual PD fluid to drain. To this end, the control unit in one embodiment also knows how much fresh PD fluid has been drained from each of the PD fluid containers or bags over the course of treatment.

In various embodiments, one of the PD fluid containers or bags may hold icodextrin, which is formulated to be delivered to the patient at the end of treatment as a last fill. The icodextrin remains inside the patient until the next nightly treatment or until an intermediary exchange, such as a midday exchange. The last fill of icodextrin is the last procedure performed by PD machine or cycler for the treatment, so there is no subsequent patient dwell. Here, the control unit may be configured to attempt to pump as much icodextrin as possible to the patient during the last fill. The control unit may then cause any residual icodextrin remaining at the end of the last fill to be pumped to drain. The patient or caregiver may alternatively shut down the PD machine or cycler at the end of treatment and transport the PD fluid container or bag with any residual icodextrin (but all other containers or bags empty or virtually empty) for disposal.

A third PD treatment improvement feature of the present disclosure, which may be provided alternatively or in addition to one or both of the drip prevention feature and the bag empty feature, involves making sure that the patient is connected to the patient line before beginning a new patient drain. The patient during a patient dwell may disconnect from the dual lumen patient line, e.g., by disconnecting the patient's transfer set from a disposable filter set described herein. It is contemplated that the user interface provide a button or input that allows the patient to inform the control unit of the PD machine or cycler that the patient is disconnected from the machine. But even if such an input is provided, the patient may forget to press or actuate the input. In an alternative embodiment, such an input is not provided and the patient is relied upon to reconnect to dual lumen patient line prior to the beginning of the next patient drain.

In any of the scenarios discussed above, the patient may not be present and connected to dual lumen patient line when the next patient drain is initiated. If so, and if the patient upon disconnecting from the PD machine or cycler connects the distal end of the dual lumen patient line to a patient line connector at the machine, then a negative pressure applied by the PD fluid pump during a subsequent patient drain will result in a negative pressure spike or increase as the negative pressure extends to the closed fresh PD fluid side of the fluid lines within the PD machine or cycler. If the patient upon disconnecting from PD machine or cycler instead leaves dual lumen patient line unattended (dangling), then a negative pressure applied by PD fluid pump during a subsequent patient drain will result in air being drawn into the used PD fluid lumen of the dual lumen patient line.

To prevent either situation above from occurring, it is contemplated that the control unit of the PD machine or cycler of the present disclosure cause the PD fluid pump to pump a small amount of fresh PD fluid (which may be heated) towards the patient along the dual lumen patient line. The small amount of fresh PD fluid pumped may be on the order of one to ten, e.g., five milliliters ("ml") and may be pumped down the fresh PD fluid lumen when dual lumen patient line is employed. Alternatively or additionally, since the next treatment procedure is a patient drain, and only a small amount of PD fluid is pumped, the control unit may cause a small amount of used PD fluid to be pumped to the used PD fluid lumen of dual lumen patient line.

If the patient is properly connected to the disposable filter set and dual lumen patient line when the small amount of fresh/used PD fluid is pushed towards the patient, an output to the control unit from the one or more pressure sensor is characteristic of the patient being properly connected. The output may for example be the same as or similar to the output sensed during a patient fill. Upon determining that the output from the one or more pressure sensor is characteristic of the patient being properly connected for treatment, control unit 100 causes the next patient drain to be commenced.

If the patient is not properly connected to the disposable filter set and dual lumen patient line when the small amount of fresh/used PD fluid is pushed towards the patient, and when the distal end of the dual lumen patient line is parked at and connected to the patient line connector at the machine, an output to the control unit from the one or more pressure sensor shows a positive pressure increase that is characteristic of the distal end of the dual lumen patient line being connected to the patient line connector. Here, the small amount of fresh/used PD fluid added to the dual lumen patient line and the internal PD fluid lines of the PD machine or cycler will result in a characteristic increase of positive pressure as the additional fluid is pressed into the closed internal lines of the PD machine or cycler. Upon determining that the output from the one or more pressure sensor is characteristic of the dual lumen patient line being connected improperly to the patient line connector, the control unit causes the user interface to audibly, visually or audiovisually alarm or alert and notify the patient that the patient line needs to be removed from the PD machine or cycler and to be connected to the disposable filter set (which is connected to the patient's transfer set).

If the patient is not properly connected to the disposable filter set and dual lumen patient line when the small amount of fresh/used PD fluid is pushed towards the patient, and wherein the distal end of the dual lumen patient line has been left unattended and unconnected by the patient, then an output to the control unit from one or more pressure sensor shows a different pressure than if the patient line is connected to the patient. Upon determining that the output from one or more pressure sensor is characteristic of the dual lumen patient line being left unattended and unconnected by the patient, the control unit causes the user interface to audibly, visually or audiovisually alarm or alert and notify the patient that the patient line needs to be connected to the disposable filter set (which is connected to the patient's transfer set).

In light of the disclosure set forth herein, and without limiting the disclosure in any way, in a first aspect of the present disclosure, which may be combined with any other aspect, or portion thereof, a peritoneal dialysis ("PD") system includes a housing; a PD fluid pump housed by the housing; a reusable patient line extending from the housing, the reusable patient line including a distal end configured to be connected to a patient line connector provided by the housing; at least one reusable PD fluid line extending from the housing, the at least one reusable PD fluid line including a distal end configured to be connected to a PD fluid line connector provided by the housing; and a control unit configured to cause, prior to any of the lines being connected for treatment, the PD fluid pump to apply a negative pressure to at least one of the reusable patient line or the at least one reusable PD fluid line when connected, respectively, to the patient line connector and the PD fluid line connector.

In a second aspect of the present disclosure, which may be combined with any other aspect, or portion thereof, the reusable patient line is a dual lumen patient line including a fresh PD fluid lumen and a used PD fluid lumen, and wherein the negative pressure is applied to at least one of the fresh PD fluid lumen and the used PD fluid lumen.

In a third aspect of the present disclosure, which may be combined with any other aspect, or portion thereof, the negative pressure is applied to the fresh PD fluid lumen by running the PD fluid pump in a reverse to treatment direction, and the negative pressure is applied to the used PD fluid lumen by running the PD fluid pump in the treatment direction.

In a fourth aspect of the present disclosure, which may be combined with any other aspect, or portion thereof, the PD system includes a plurality of PD fluid line valves, and wherein the negative pressure is applied to a plurality of the PD fluid lines via the PD fluid pump and by sequentially opening the plurality of PD fluid line valves.

In a fifth aspect of the present disclosure, which may be combined with any other aspect, or portion thereof, the negative pressure is from −5 kPa (−0.73 psig) to −15 kPa (−2.2 psig).

In a sixth aspect of the present disclosure, which may be combined with any other aspect, or portion thereof, the reusable patient line is connected to the patient line connector and the at least one reusable PD fluid line is connected to at least one PD fluid line connector during a disinfection sequence, and wherein the negative pressure is applied automatically after the disinfection sequence.

In a seventh aspect of the present disclosure, which may be combined with any other aspect, or portion thereof, the housing houses internal PD fluid lines, the reusable patient line and the at least one reusable PD fluid line forming a closed PD fluid loop with the internal PD fluid lines for the disinfection sequence.

In an eighth aspect of the present disclosure, which may be combined with any other aspect, or portion thereof, the PD system includes a user interface, the control unit further configured to cause the user interface to provide a message to wait to remove the reusable patient line and the at least one reusable PD fluid line from the housing until a line disconnection preparation sequence is completed.

In a ninth aspect of the present disclosure, which may be combined with any other aspect, or portion thereof, the PD system includes a user interface, the control unit further configured to cause the user interface to provide a message that the reusable patient line and the at least one reusable PD fluid line are ready to be removed from the housing.

In a tenth aspect of the present disclosure, which may be combined with any other aspect, or portion thereof, the user interface is further configured to provide a moving graphic illustrating a proper way for the distal end of the reusable patient line or the reusable PD fluid line to be removed from the housing.

In an eleventh aspect of the present disclosure, which may be combined with any other aspect, or portion thereof, the negative pressure causes at least one of the reusable patient line or the at least one reusable PD fluid line to collapse prior to removal from the housing and to expand after removal from the housing, which tends to hold PD fluid within at least one of the reusable patient line or the at least one reusable PD fluid line.

In a twelfth aspect of the present disclosure, which may be combined with any other aspect, or portion thereof, the PD system includes a disposable filter set for connection to the reusable patient line distal end when removed from the housing.

In a thirteenth aspect of the present disclosure, which may be combined with any other aspect, or portion thereof, the PD system includes at least one PD fluid container for connection to the at least one reusable PD fluid line distal end when removed from the housing.

In a fourteenth aspect of the present disclosure, which may be combined with any other aspect, or portion thereof, at least one of the patient line connector or the at least one PD fluid line connector is horizontally disposed relative to the housing.

In a fifteenth aspect of the present disclosure, which may be combined with any other aspect, or portion thereof, the control unit is further configured to cause, prior to any of the lines being connected for treatment, at least one valve to lock the negative pressure at the distal end of the reusable patient line.

In a sixteenth aspect of the present disclosure, which may be combined with any other aspect, or portion thereof, the control unit is further configured to cause, prior to any of the lines being connected for treatment, at least one valve to lock the negative pressure at the distal end of the at least one PD fluid line.

In a seventeenth aspect of the present disclosure, which may be combined with any other aspect, or portion thereof, a peritoneal dialysis ("PD") machine includes a housing; a PD fluid pump housed by the housing; a reusable patient line extending from the housing, the reusable patient line including a distal end configured to be connected so that the reusable patient line is placed in fluid communication with at least one internal PD fluid line located within the housing; at least one reusable PD fluid line extending from the housing, the at least one reusable PD fluid line including a distal end configured to be connected so that the at least one PD fluid line is placed in fluid communication with the at least one internal PD fluid line; and a control unit configured to cause, prior to any of the lines being connected for treatment, the PD fluid pump to apply a negative pressure to at least one of the reusable patient line or the at least one reusable PD fluid line when connected for fluid communication with the at least one internal PD fluid line.

In an eighteenth aspect of the present disclosure, which may be combined with any other aspect, or portion thereof, the reusable patient line is placed in fluid communication with at least one internal PD fluid line and the at least one reusable PD fluid line is placed in fluid communication with the at least one internal PD fluid line during a disinfection sequence, and wherein the negative pressure is applied automatically after the disinfection sequence.

In a nineteenth aspect of the present disclosure, which may be combined with any other aspect, or portion thereof, the control unit is further configured to cause, prior to any of the lines being connected for treatment, at least one valve to lock the negative pressure at the distal end of the reusable patient line.

In a twentieth aspect of the present disclosure, which may be combined with any other aspect, or portion thereof, the control unit is further configured to cause, prior to any of the lines being connected for treatment, at least one valve to lock the negative pressure at the distal end of the at least one PD fluid line.

In a twenty-first aspect of the present disclosure, which may be combined with any other aspect, or portion thereof, a peritoneal dialysis ("PD") system includes a plurality of PD fluid containers; and a PD machine including a housing, a PD fluid pump housed by the housing, and a control unit configured to cause the PD fluid pump, during a patient dwell, to remove residual PD fluid from at least one of the plurality of PD fluid containers.

In a twenty-second aspect of the present disclosure, which may be combined with any other aspect, or portion thereof, the PD system includes a separate PD fluid line extending from the housing to each of the PD fluid containers, and wherein the residual PD fluid is pumped through the at least one respective PD fluid line.

In a twenty-third aspect of the present disclosure, which may be combined with any other aspect, or portion thereof, the PD fluid lines are reusable.

In a twenty-fourth aspect of the present disclosure, which may be combined with any other aspect, or portion thereof, the plurality of PD fluid containers are in fluid communication with a disposable pumping portion operable with the PD fluid pump.

In a twenty-fifth aspect of the present disclosure, which may be combined with any other aspect, or portion thereof, the control unit is configured to cause, during a final patient dwell, the PD fluid pump to remove residual PD fluid from a plurality of PD fluid containers.

In a twenty-sixth aspect of the present disclosure, which may be combined with any other aspect, or portion thereof, the PD machine includes a PD fluid valve for each PD fluid container, and wherein the control unit is configured to sequence open the PD valve for the respective PD fluid container while residual PD fluid is pumped from the respective PD fluid container during the final patient dwell.

In a twenty-seventh aspect of the present disclosure, which may be combined with any other aspect, or portion thereof, the control unit is further configured such that if one of the PD fluid containers is a last fill container, the PD fluid pump is caused to perform a last patient fill using last fill PD fluid from the last fill container after a final patient drain following the final patient dwell.

In a twenty-eighth aspect of the present disclosure, which may be combined with any other aspect, or portion thereof, the control unit is further configured to predetermine for each PD fluid container from which residual PD fluid is pumped, that the PD fluid container has less than a fill volume's worth of residual PD fluid.

In a twenty-ninth aspect of the present disclosure, which may be combined with any other aspect, or portion thereof, the control unit is configured to cause the residual PD fluid to be pumped from the at least one of the plurality of PD fluid containers to drain.

In a thirtieth aspect of the present disclosure, which may be combined with any other aspect, or portion thereof, the drain is a drain container or house drain.

In a thirty-first aspect of the present disclosure, which may be combined with any other aspect, or portion thereof, the control unit is configured to cause the residual PD fluid to be pumped from the at least one of the plurality of PD fluid containers to a different PD fluid container.

In a thirty-second aspect of the present disclosure, which may be combined with any other aspect, or portion thereof, the control unit is configured to cause the PD fluid pump, during a plurality of patient dwells, to remove residual PD fluid from at least one of the plurality of PD fluid containers.

In a thirty-third aspect of the present disclosure, which may be combined with any other aspect, or portion thereof, the PD machine includes a PD fluid valve for each PD fluid container, and wherein the control unit is configured to sequence open the PD valve for the respective PD fluid container while residual PD fluid is pumped from the respective PD fluid container during one of the patient dwells.

In a thirty-fourth aspect of the present disclosure, which may be combined with any other aspect, or portion thereof, the control unit is further configured such that if one of the PD fluid containers is a last fill container, the PD fluid pump is caused to perform a last patient fill using last fill PD fluid from the last fill container after a final patient drain.

In a thirty-fifth aspect of the present disclosure, which may be combined with any other aspect, or portion thereof, the control unit is further configured to predetermine for each PD fluid container from which residual PD fluid is pumped, that the PD fluid container has less than a fill volume's worth of residual PD fluid.

In a thirty-sixth aspect of the present disclosure, which may be combined with any other aspect, or portion thereof, a method for aiding the transport of a peritoneal dialysis ("PD") disposable item after treatment, the method including causing a PD fluid pump to pump PD fluid from a PD fluid container to a patient over a patient fill; and during a subsequent patient dwell, causing the PD fluid pump to remove residual PD fluid from the PD fluid container so that the residual PD fluid does not have to be transported after treatment.

In a thirty-seventh aspect of the present disclosure, which may be combined with any other aspect, or portion thereof, the method includes determining that an amount of residual PD fluid is less than a prescribed fill volume amount before pumping the residual PD fluid from the PD fluid container.

In a thirty-eighth aspect of the present disclosure, which may be combined with any other aspect, or portion thereof, the method includes pumping the residual PD fluid from the PD fluid container to drain or to another PD fluid container.

In a thirty-ninth aspect of the present disclosure, which may be combined with any other aspect, or portion thereof, the subsequent patient dwell is a final patient dwell, and which includes causing the PD fluid pump to remove residual PD fluid from a plurality of PD fluid containers during the final patient dwell.

In a fortieth aspect of the present disclosure, which may be combined with any other aspect, or portion thereof, the subsequent patient dwell is a first patient dwell, and which includes causing the PD fluid pump to remove residual PD fluid from a second PD fluid container during a second patient dwell.

In a forty-first aspect of the present disclosure, which may be combined with any other aspect, or portion thereof, the method includes causing the PD fluid pump to pump a last fill PD fluid to a patient after removing residual PD fluid from each of the other PD fluid containers.

In a forty-second aspect of the present disclosure, which may be combined with any other aspect, or portion thereof, a peritoneal dialysis ("PD") system includes a housing; a PD fluid pump housed by the housing; a pressure sensor positioned and arranged to sense a pressure of PD fluid pumped by the PD fluid pump; a patient line in fluid communication with the PD fluid pump, the patient line configured to be placed in fluid communication with a patient's transfer set to perform a PD treatment; and a control unit configured to (i) cause the PD fluid pump, prior to a patient drain, to pump an amount of PD fluid into the patient line, (ii) record an output from the pressure sensor due to the pumped amount of PD fluid, and (iii) determine if the patient line is in fluid communication with the patient's transfer set based on the output from the pressure sensor.

In a forty-third aspect of the present disclosure, which may be combined with any other aspect, or portion thereof, the control unit is further configured to cause the patient drain to begin if the patient line is determined to be in fluid communication with the patient's transfer set based on the output from the pressure sensor.

In a forty-fourth aspect of the present disclosure, which may be combined with any other aspect, or portion thereof, the control unit is further configured to cause a visual, audio or audiovisual message to be provided if the patient line is determined not to be in fluid communication with the patient's transfer set based on the output from the pressure sensor.

In a forty-fifth aspect of the present disclosure, which may be combined with any other aspect, or portion thereof, after or in combination with the message, the control unit is further configured to request confirmation that the patient line has been placed in fluid communication with the patient's transfer set.

In a forty-sixth aspect of the present disclosure, which may be combined with any other aspect, or portion thereof, the control unit is further configured, upon receiving confirmation that the patient line has been placed in fluid communication with the patient's transfer set, to (i) cause the PD fluid pump, prior to the patient drain, to pump a second amount of PD fluid into the patient line, (ii) record a second output from the pressure sensor due to the second pumped amount of PD fluid, and (iii) determine if the patient line is in fluid communication with the patient's transfer set based on the second output from the pressure sensor.

In a forty-seventh aspect of the present disclosure, which may be combined with any other aspect, or portion thereof, the control unit is further configured to determine a location of a distal end of the patient line based on the output from the pressure sensor if the patient line is determined not to be in fluid communication with the patient's transfer set.

In a forty-eighth aspect of the present disclosure, which may be combined with any other aspect, or portion thereof, one determined location of the distal end of the patient line is being connected to a patient line connector at the housing, and wherein the control unit is further configured to cause a visual, audio or audiovisual prompt to be provided urging disconnection from the patient line connector at the housing and reconnection to a connector at the patient.

In a forty-ninth aspect of the present disclosure, which may be combined with any other aspect, or portion thereof, one determined location of the distal end of the patient line is being left unconnected, and wherein the control unit is further configured to cause a visual, audio or audiovisual prompt to be provided urging connection of the distal end to a connector at the patient.

In a fiftieth aspect of the present disclosure, which may be combined with any other aspect, or portion thereof, the amount of PD fluid is one to ten, e.g., five milliliters ("ml").

In a fifty-first aspect of the present disclosure, which may be combined with any other aspect, or portion thereof, the pressure sensor includes a plurality of pressure sensors, and wherein the control unit is configured to determine if the patient line is in fluid communication with the patient's transfer set based on a plurality of outputs from the plurality of pressure sensors.

In a fifty-second aspect of the present disclosure, which may be combined with any other aspect, or portion thereof, the patient line is reusable and extends from the housing.

In a fifty-third aspect of the present disclosure, which may be combined with any other aspect, or portion thereof, the patient line is disposable and is in fluid communication with a disposable pumping portion operable with the PD fluid pump.

In a fifty-fourth aspect of the present disclosure, which may be combined with any other aspect, or portion thereof, the patient line is configured to be placed in fluid communication with a patient's transfer set via a disposable filter located between the patient line and the patient's transfer set.

In a fifty-fifth aspect of the present disclosure, which may be combined with any other aspect, or portion thereof, the patient line is a dual lumen patient line and wherein pumping an amount of PD fluid into the patient line includes pumping the amount into one or both of a fresh or used PD fluid lumen of the dual lumen patient line.

In a fifty-sixth aspect of the present disclosure, which may be combined with any other aspect, or portion thereof, a method for discouraging commencement of a patient drain with an unconnected or improperly connected patient line, the method including causing an amount of PD fluid to be pumped into a patient line prior to a patient drain; measuring a resulting pressure from the amount of PD fluid pumped into the patient line; determining from the resulting pressure if the patient line is in fluid communication with the patient's transfer set; and causing the patient drain to begin if the patient line is determined to be in fluid communication with the patient's transfer set.

In a fifty-seventh aspect of the present disclosure, which may be combined with any other aspect, or portion thereof, the method includes determining a location of a distal end of the patient line from the resulting pressure if the patient line is determined not to be in fluid communication with the patient's transfer set.

In a fifty-eighth aspect of the present disclosure, which may be combined with any other aspect, or portion thereof, the method includes prompting a connection of the patient line based on the determined location of the distal end.

In a fifty-ninth aspect of the present disclosure, which may be combined with any other aspect, or portion thereof, the method includes repeating the causing, measuring, determining and causing steps after receiving a confirmation that the patient line has been placed in fluid communication with the patient's transfer set.

In a sixtieth aspect of the present disclosure, which may be combined with any other aspect, or portion thereof, any of the features, functionality and alternatives described in connection with any one or more of FIGS. 1 to 5 may be combined with any of the features, functionality and alternatives described in connection with any other of FIGS. 1 to 5.

In light of the above aspects and present disclosure set forth herein, it is an advantage of the present disclosure to provide an improved dialysis system and method, which operates to prevent leaks when gaining access to presterilized, e.g., bagged dialysis fluid.

It is another advantage of the present disclosure to provide a dialysis system configured to detect and take appropriate action when a currently used container or bag runs out of dialysis fluid during treatment, e.g., during a PD patient fill.

It is a further advantage of the present disclosure to provide a PD system configured to automatically remove residual PD fluid during one or more patient dwell, reducing the burden of post-treatment disposable removal and transport.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the improvements or advantages listed herein, and it is expressly contemplated to claim individual advantageous embodiments separately. In particular, the system of the present disclosure may have any one or more or all of the drip prevention structure and methodology, PD fluid container emptying structure and methodology and patient connection before drain check structure and methodology described herein. Moreover, it should be noted that the language used in the specification has been selected principally for readability and instructional purposes, and not to limit the scope of the inventive subject matter.

DETAILED DESCRIPTION

System Overview

Figure 1:
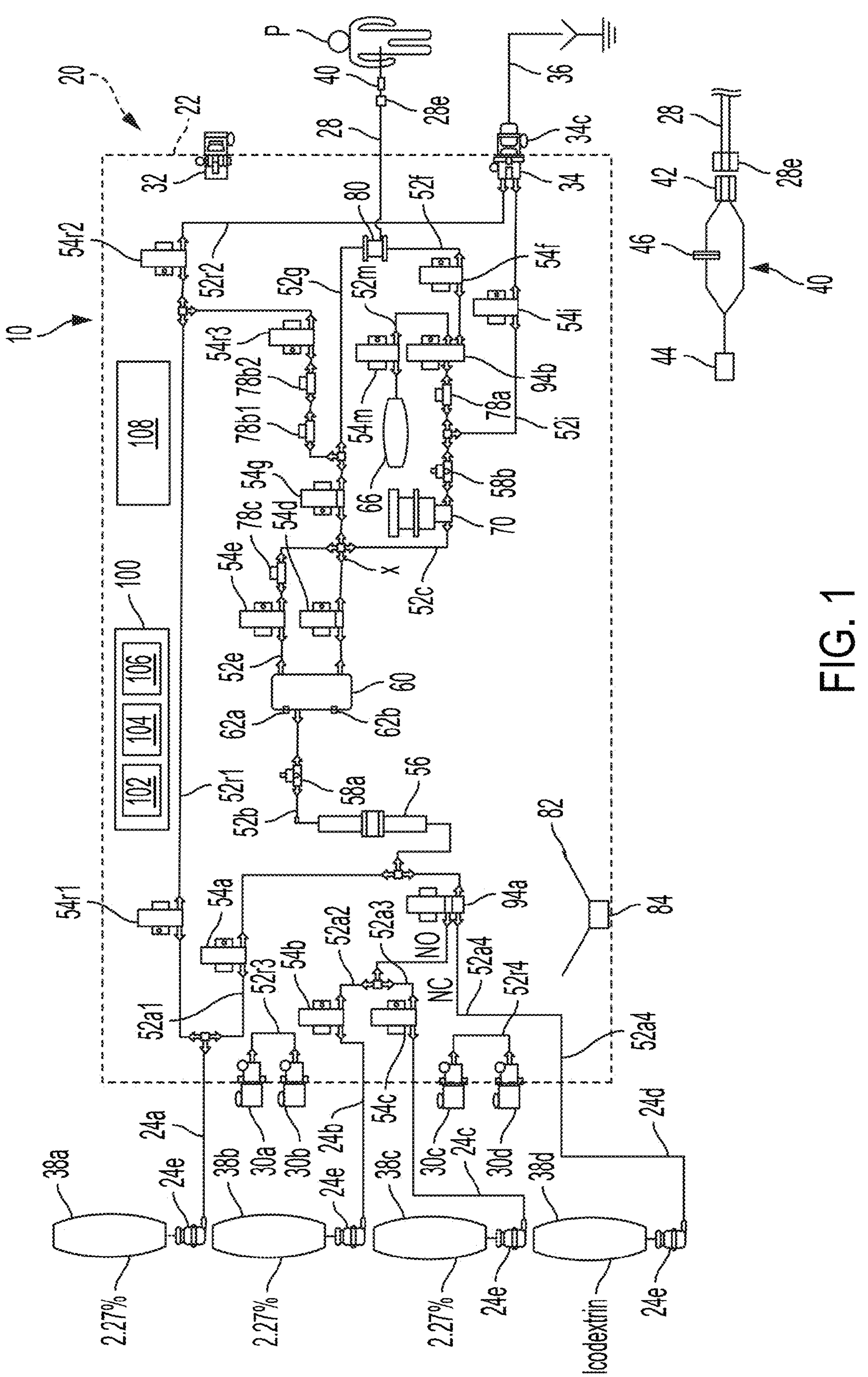
FIG. 1 is a fluid flow schematic of one embodiment for a medical fluid, e.g., PD fluid, system including the enhanced features of the present disclosure.

Referring now to the drawings and in particular to FIG. 1, a medical system having the enhanced features of the present disclosure is illustrated via peritoneal dialysis ("PD") system 10. System 10 includes a PD machine or cycler 20 and a control unit 100 having one or more processor 102, one or more memory 104, video controller 106 and user interface 108. User interface 108 may alternatively or additionally be a remote user interface, e.g., via a tablet or smartphone. Control unit 100 may also include a transceiver and a wired or wireless connection to a network (not illustrated), e.g., the internet, for sending treatment data to and receiving prescription instructions/changes from a doctor's or clinician's server interfacing with a doctor's or clinician's computer. Control unit 100 in an embodiment controls all electrical fluid flow and heating components of system 10 and receives outputs from all sensors of system 10. System 10 in the illustrated embodiment includes durable and reusable components that contact fresh and used PD fluid, which necessitates that PD machine or cycler 20 be disinfected between treatments, e.g., via heat disinfection.

System 10 in FIG. 1 includes an inline resistive heater 56, reusable supply lines or tubes **52*a*1 to 52*a*4 and 52*b*, air trap 60 operating with respective upper and lower level sensors 62*a* and 62*b*, air trap valve 54*d*, vent valve 54*e* located along vent line 52*e*, reusable line or tubing 52*c*, PD fluid pump 70, temperature sensors 58*a* and 58*b*, pressure sensors 78*a*, 78*b*1, 78*b*2 and 78*c*, reusable patient tubing or lines 52*f* and 52*g* having respective valves 54*f* and 54*g*, dual lumen patient line 28, a hose reel 80 for retracting patient line 28, reusable drain tubing or line 52*i* extending to drain line connector 34 and having a drain line valve 54*i*, and reusable recirculation disinfection tubing or lines 52*r*1 and 52*r*2 operating with respective disinfection valves 54*r*1 and 54*r*2. A third recirculation or disinfection tubing or line 52*r*3 extends between disinfection or PD fluid line connectors 30*a* and 30*b* for use during disinfection. A fourth recirculation or disinfection tubing or line 52*r*4 extends between disinfection connectors 30*c* and 30*d*** for use during disinfection.

System 10 further includes PD fluid containers or bags **38*a* to 38*c* (e.g., holding the same or different formulations of PD fluid), which connect to distal ends 24*e* of reusable PD fluid lines 24*a* to 24*c*, respectively. System 10*d* further includes a fourth PD fluid container or bag 38*d* that connects to a distal end 24*e* of reusable PD fluid line 24*d*. Fourth PD fluid container or bag 38*d* may hold the same or different type (e.g., icodextrin) of PD fluid than provided in PD fluid containers or bags 38*a* to 38*c*. Reusable PD fluid lines 24*a* to 24*d* extend in one embodiment through apertures (not illustrated) defined or provided by housing 22 of cycler 20**.

System 10 in the illustrated embodiment includes four disinfection or PD fluid line connectors **30*a* to 30*d* for connecting to distal ends 24*e* of reusable PD fluid lines 24*a* to 24*d*, respectively, during disinfection. System 10 also provides a patient line connector 32 that includes an internal lumen, e.g., a U-shaped lumen, which for disinfection directs fresh or used dialysis fluid from one PD fluid lumen of a connected distal end 28*e* of dual lumen patient line 28 into the other PD fluid lumen. Reusable supply tubing or lines 52*a*1 to 52*a*4 communicate with reusable supply lines 24*a* to 24*d*, respectively. Reusable supply tubing or lines 52*a*1 to 52*a*3 operate with valves 54*a* to 54*c*, respectively, to allow PD fluid from a desired PD fluid container or bag 38*a* to 38*c* to be pulled into cycler 20. Three-way valve 94*a*** in the illustrated example allows for control unit 100 to select between (i) 2.27% (or other) glucose dialysis fluid from container or bag 38*b* or 38*c* and (ii) icodextrin from container or bag 38*d*. In the illustrated embodiment, icodextrin from container or bag 38*d* is connected to the normally closed port of three-way valve 94*a*.

System 10 is constructed in one embodiment such that drain line 52*i* during a patient fill is fluidly connected downstream from PD fluid pump 70. In this manner, if drain valve 54*i* fails or somehow leaks during the patient fill of patient P, fresh PD fluid is pushed down disposable drain line 36 instead of used PD fluid potentially being pulled into pump 70. Disposable drain line 36 is in one embodiment removed for disinfection, wherein drain line connector 34 is capped via a cap 34*c* to form a closed disinfection loop. PD fluid pump 70 may be an inherently accurate pump, such as a piston pump, or less accurate pump, such as a gear pump that operates in cooperation with a flowmeter (not illustrated) to control fresh and used PD fluid flowrate and volume.

System 10 may further include a leak detection pan 82 located at the bottom of housing 22 of cycler 20 and a corresponding leak detection sensor 84 outputting to control unit 100. In the illustrated example, system 10 is provided with an additional pressure sensor 78*c* located upstream of PD fluid pump 70, which allows for the measurement of the suction pressure of pump 70 to help control unit 100 more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c*.

System 10 in the example of FIG. 1 includes redundant pressure sensors 78*b*1 and 78*b*2, the output of one of which is used for pump control, as discussed herein, while the output of the other pressure sensor is a safety or watchdog output to make sure the control pressure sensor is reading accurately. Pressure sensors 78*b*1 and 78*b*2 are located along a line including a third recirculation valve 54*r*3. System 10 may further employ one or more cross, marked via an X in FIG. 1, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve 94*b* via a citric acid valve 54*m* located along a citric acid line 52*m*. Citric acid line 52*m* is connected in one embodiment to the normally closed port of second three-way valve 94*b*, so as to provide redundant valves between citric acid container or bag 66 and the PD fluid circuit during treatment. The redundant valves ensure that no citric (or other) acid reaches the treatment fluid lines during treatment. Citric (or other) acid is used instead during disinfection.

Control unit 100 in an embodiment uses feedback from any one or more of pressure sensors 78*a* to 78*c* to enable PD machine 20 to deliver fresh, heated PD fluid to the patient at, for example, 14 kPa (2.0 psig) or higher. The pressure feedback is used to enable PD machine 20 to remove used PD fluid or effluent from the patient at, for example, between −5 kPa (−0.73 psig) and −15 kPa (−2.2 psig), such as −9 kPa (−1.3 psig) or higher (more negative). The pressure feedback may be used in a proportional, integral, derivative ("PID") pressure routine for pumping fresh and used PD fluid at a desired positive or negative pressure.

Inline resistive heater 56 under control of control unit 100 is capable of heating fresh PD fluid to body temperature, e.g., 37° C., for delivery to patient P at a desired flowrate. Control unit 100 in an embodiment uses feedback from temperature sensor 58*a* in a PID temperature routine for pumping fresh PD fluid to patient P at a desired temperature.

FIG. 1 also illustrates that system 10 includes and uses a disposable filter set 40, which communicates fluidly with the fresh and used PD fluid lumens of dual lumen patient line 28. Disposable filter set 40 includes a disposable connector 42 that connects to a distal end 28*e* of reusable patient line 28. Disposable filter set 40 also includes a connector 44 that connects to the patient's transfer set. Disposable filter set 40 further includes a sterilizing grade filter membrane 46 that further filters fresh PD fluid. Disposable filter set 40 is provided in one embodiment as a last chance filter for PD machine 20, which has been heat disinfected between treatments. Any pathogens that may remain after disinfection, albeit unlikely, are filtered from the PD fluid via the sterilizing grade filter membrane 46 of disposable filter set 40.

FIG. 1 illustrates system 10 setup for treatment with PD fluid containers or bags 38*a* to 38*d* connected via reusable, flexible PD fluid lines 24*a* to 24*d*, respectively. Dual lumen patient line 28 is connected to patient P via disposable filter set 40. Disposable drain line 36 is connected to drain line connector 34. In FIG. 1, PD machine or cycler 20 of system 10 is configured to perform multiple patient drains, patient fills, patient dwells, and a priming procedure, as part of or in preparation for treatment.

Figure 2:
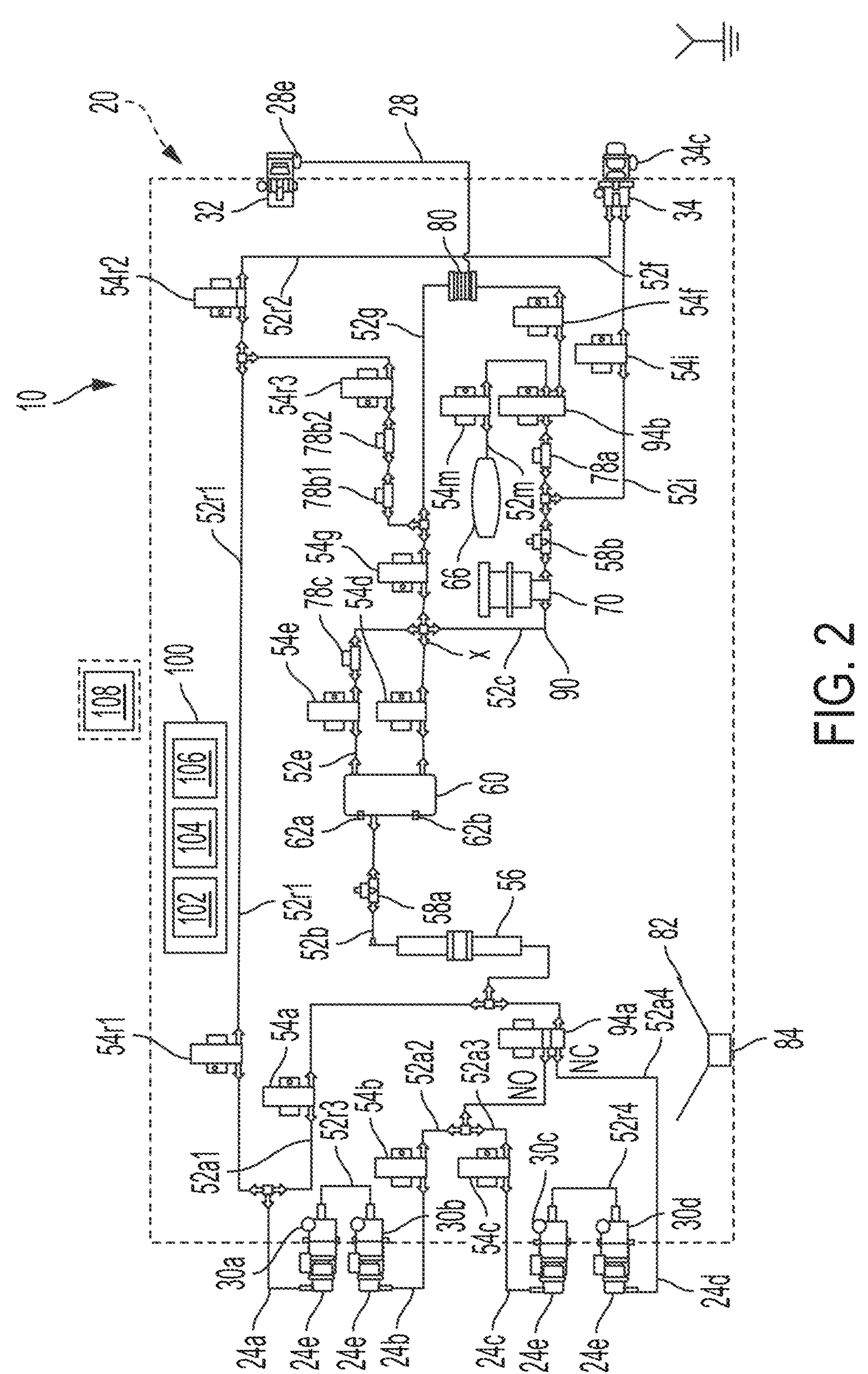
FIG. 2 is a fluid flow schematic of one embodiment for a medical fluid, e.g., PD fluid, system of FIG. 1, which has been rearranged for disinfection.

FIG. 2 illustrates system 10 in a disinfection mode. PD fluid containers or bags 38*a* to 38*d* are removed and flexible PD fluid lines 24*a* to 24*d* are plugged instead in a sealed manner into disinfection or PD fluid line connectors 30*a* to 30*d*, respectively. Reusable Dual lumen patient line 28 is disconnected from disposable filter set 40 (which is discarded), and distal end 28*e* of dual lumen patient line 28 is plugged sealingly into patient line connector 32. Disposable drain line 36 is removed from drain line connector 34 and discarded. Drain line connector 34 is capped via cap 34*c* to form a closed disinfection loop 90. PD machine or cycler 20 of system 10 in FIG. 2 is configured to perform a disinfection sequence, e.g., a heat disinfection sequence in which fresh PD fluid is heated via inline heater 56 to a disinfection temperature, e.g., 70° C. to 90° C. PD fluid pump 70 circulates the heated PD fluid closed disinfection loop 90 for an amount of time needed to properly disinfect the fluid components and lines of the disinfection loop.

Drip Prevention

Referring still to FIG. 2, it is contemplated in one embodiment to leave the disinfection fluid within PD machine or cycler 20 until a next treatment. Flexible PD fluid lines 24*a* to 24*d*, disinfection or PD fluid line connectors 30*a* to 30*d*, dual lumen patient line 28, and patient line connector 32 are accordingly wet upon disconnection from PD machine or cycler 20. When, at the start of a new treatment, the patient or caregiver (i) removes distal ends 24*e* of reusable PD fluid lines 24*a* to 24*d* respectively from connectors 30*a* to 30*d*, and (ii) removes distal end 28*e* of dual lumen patient line 28 from patient line connector 32, there is a risk that fluid may leak from the distal ends 24*e*, 28*e* before a reconnection to (i) new PD fluid containers or bags 38*a* to 38*d* (for PD fluid lines) and (ii) a new disposable filter set 40 (for the patient line) can be made.

To prevent dripping or leaking, control unit 100 of PD machine or cycler 20 is configured, in one embodiment, to open the appropriate valves and cause PD fluid pump 70 to apply negative pressure to reusable PD fluid lines 24*a* to 24*d* and dual lumen patient line 28 prior to the patient or caregiver removing any of those lines during treatment setup, which cause the flexible lines under negative pressure to collapse slightly. In this way, when the patient or caregiver (i) removes distal ends 24*e* of reusable PD fluid lines 24*a* to 24*d* respectively from PD fluid line connectors 30*a* to 30*d*, and (ii) removes distal end 28*e* of dual lumen patient line 28 from patient line connector 32, the flexible PD fluid lines 24*a* to 24*c* and the dual lumen patient line 28 expand, causing a small amount of air to be sucked into the ends of the lines, preventing spillage or dripping.

Regarding dual lumen patient line 28, it is contemplated to program control unit 100 to place either or both of the fresh and used lumens of dual lumen patient line 28 under negative pressure. Viewing FIG. 2, it is contemplated for control unit 100 to place the fresh PD fluid lumen of dual lumen patient line 28 under negative pressure by causing fresh PD fluid valve 54*f* and vent valve 54*e* to open and leaving three-way valve 94*b* in its normally closed state (all other valves may be closed). Control unit 100 then causes PD fluid pump 70 to run in reverse and apply negative pressure to the disinfection fluid, e.g., PD fluid, located within fresh PD fluid line 52*f* and the fresh PD fluid lumen of dual lumen patient line 28. When the negative pressure reaches a desired or set negative pressure, e.g., between −5 kPa (−0.73 psig) and −15 kPa (−2.2 psig), such as −9 kPa (−1.3 psig), as measured by pressure sensor 78*a* outputting to control unit 100, the control unit causes at least fresh PD fluid valve 54*f* to close and PD fluid pump 70 to stop. The closure of fresh PD fluid valve 54*f* locks the applied negative pressure in the portion of fresh PD fluid line 52*f* located downstream from fresh PD fluid valve 54*f* and the fresh PD fluid of dual lumen patient line 28 (assuming no leaks). The locked negative pressure awaits the patient or caregiver removal of patient line distal end 28*e* from patient line connector 32 during treatment setup.

Viewing FIG. 2, it is contemplated for control unit 100 to place the used PD fluid lumen of dual lumen patient line 28 under negative pressure by causing used PD fluid valve 54*g* and drain valve 54*i* to open (all other valves may be closed). Control unit 100 then causes PD fluid pump 70 to run in the normal direction and apply negative pressure to the disinfection fluid, e.g., PD fluid, located within used PD fluid line 52*g* and the used PD fluid lumen of dual lumen patient line 28. When the negative pressure reaches a desired or set negative pressure, e.g., between −5 kPa (−0.73 psig) and −15 kPa (−2.2 psig), such as −9 kPa (−1.3 psig), as measured by pressure sensor 78*b*1, 78*b*2 and/or 78*c* outputting to control unit 100, the control unit causes at least used PD fluid valve 54*g* to close and PD fluid pump 70 to stop. The closure of used PD fluid valve 54*g* locks the applied negative pressure in the portion of used PD fluid line 52*g* located upstream from used PD fluid valve 54*g* and the used PD fluid of dual lumen patient line 28 (assuming no leaks). The locked negative pressure awaits the patient or caregiver removal of patient line distal end 28*e* from patient line connector 32 during treatment setup.

Viewing FIG. 2, it is contemplated for control unit 100 to place reusable PD fluid line 24*a* under negative pressure by causing valves 54*a*, 54*d* and drain valve 54*i* to open (all other valves may be closed). Control unit 100 then causes PD fluid pump 70 to run in the normal direction and apply negative pressure to the disinfection fluid, e.g., PD fluid, located within reusable PD fluid lines 24*a*. When the negative pressure reaches a desired or set negative pressure, e.g., between −5 kPa (−0.73 psig) and −15 kPa (−2.2 psig), such as −9 kPa (−1.3 psig), as measured by pressure sensor 78*c* outputting to control unit 100, the control unit causes at least PD fluid valve 54*a* to close and PD fluid pump 70 to stop. The closure of PD fluid valve 54*a* locks the applied negative pressure in the portion of PD fluid line 52*a*1 located upstream from PD fluid valve 54*a* and reusable PD fluid line 24*a* (assuming no leaks). The locked negative pressure awaits the patient or caregiver removal of PD fluid line distal end 24*e* from disinfection or PD fluid line connector 30*a*.

Viewing FIG. 2, the same procedure just described for reusable PD fluid line 24*a* is performed by control unit 100 for any one or more or all of reusable PD fluid lines 24*b*, 24*c* and 24*d*, except that (i) for reusable PD fluid line 24*b*, valve 54*b* takes the place of valve 54*a*, (ii) for reusable PD fluid line 24*c*, valve 54*c* takes the place of valve 54*a*, and (iii) for reusable PD fluid line 24*d*, toggling three-way valve 94*a* takes the place of valve 54*a*. The locked negative pressure awaits the patient or caregiver removal of any one or more or all of PD fluid line distal ends 24*e* from disinfection connectors 30*b* to 30*d*, respectively.

It is contemplated for control unit 100 during treatment setup to cause user interface 108 to audibly, visually or audiovisually (i) prompt the patient to wait to remove any of the patient line and PD fluid lines until system 10 is ready (e.g., until flexible lines 24*a* to 24*d* and 28 are placed under negative pressure) and/or (ii) prompt the patient that system 10 is ready for any of the patient line and PD fluid lines to be removed for treatment setup (e.g., flexible lines 24*a* to 24*d* and 28 have been placed under negative pressure). In this manner, the patient or caregiver is guided so that setup is performed in a manner that tends to prevent spillage and drips.

The negative pressures just described enable patient line connector 32 and disinfection connectors 30*b* to 30*d* to be mounted or disposed horizontally or substantially horizontally along housing 22 of cycler 20, which may be desirable. The patient or caregiver may then initially pull distal ends 24*e*, 28*e* horizontally off of their respective connectors and then tilt distal ends 24*e*, 28*e* vertically upward so that the disinfection fluid is cupped within the distal ends 24*e*, 28*e*. The expansion of the flexible lines 24*a* to 24*d* and 28 and the pulling of air into distal ends 24*e*, 28*e* prevents spillage during the time that the patient or caregiver removes distal ends 24*e*, 28*e* horizontally and tilts them upwardly. Distal ends 24*e*, 28*e* may then be connected and sealed to new PD fluid containers or bags 38*a* to 38*d* and disposable filter set 40, respectively, without any spillage or dripping of the disinfection fluid, e.g., PD fluid.

Figure 3:
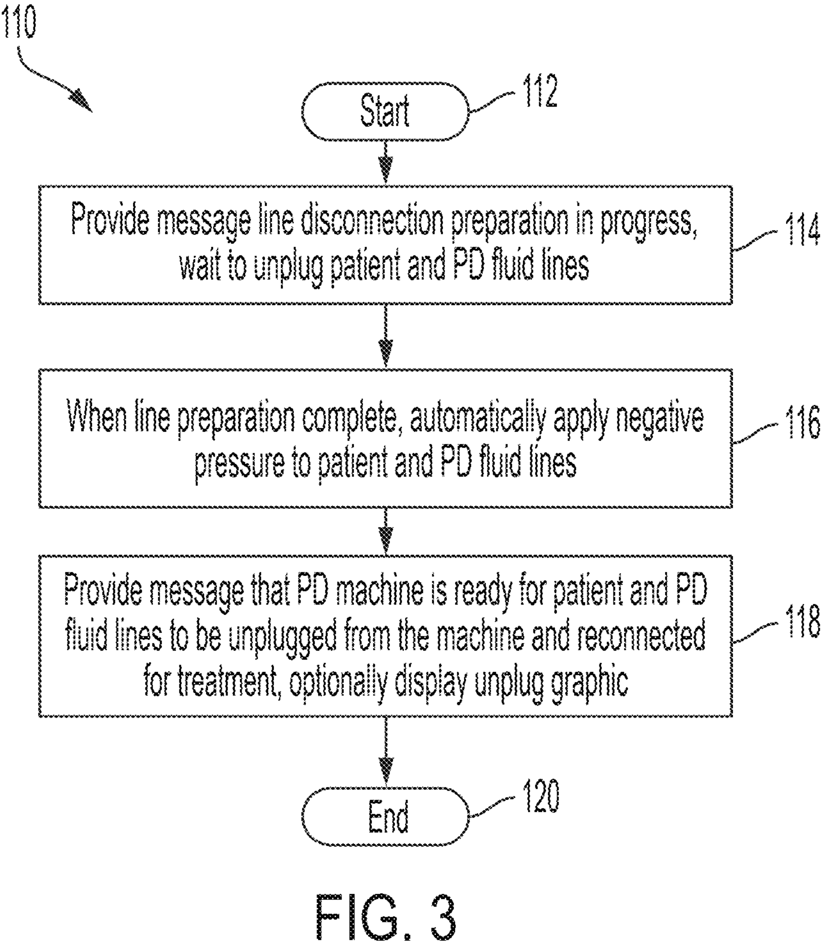
FIG. 3 is a process flow diagram summarizing one embodiment for a drip prevention method of the present disclosure.

Method 110 of FIG. 3 summarizes one embodiment for the drip prevention structure and methodology of system 10 of the present disclosure. At oval 112, method 110 begins. At block 114, control unit 100 causes user interface 108 to display (visually, audibly, or audiovisually) a message that PD machine or cycler 20 is currently running a disconnection preparation sequence and for the patient to wait to unplug flexible PD fluid lines 24*a* to 24*d* and dual lumen patient line 28 from PD machine or cycler 20 until the sequence is complete. At block 116, when the disconnection preparation sequence has been completed, control unit 100 automatically causes a vacuum to be pulled on each of flexible PD fluid lines 24*a* to 24*d* and dual lumen patient line 28 (one or both lumens), e.g., in a manner described above. At block 118, control unit 100 causes user interface 108 to display (visually, audibly, or audiovisually) a message that PD machine or cycler 20 is ready for flexible PD fluid lines 24*a* to 24*d* and dual lumen patient line 28 to be removed and connected to their respective PD fluid containers or bags 38*a* to 38*d* or to disposable filter set 40. User interface 108 may optionally display a motion picture or moving graphic of distal line ends 24*e*, 28*e* of the flexible lines being removed horizontally from PD machine or cycler 20 after which the user tips distal ends 24*e*, 28*e* up to a vertical position in which the disinfection fluid remains trapped within the distal ends 24*e*, 28*e*. At oval 120, method 110 ends.

PD Fluid Container Emptying

It is possible, and in many instances likely, that residual or leftover PD fluid remains within one, or more, or all of PD fluid containers or bags 38*a* to 38*d* at the end of treatment. The volume of a patient fill for a PD treatment is determined typically via a patient's prescription, which sets a volume of fresh PD fluid to be delivered to the patient for each patient fill. The volume of the patient fill, e.g., 1.5 to two liters, is typically less than the volume of the PD fluid container or bag, e.g., two liters. Based on these volumes, there tends to be some fresh PD fluid leftover in the container or bag.

Normally, the patient or caregiver either has to wait after treatment while the residual PD fluid is drained or has to forgo draining and transport the bags with the remaining fluid for disposal. The residual fluid adds weight and potential spillage and mess to the bag disposal. Viewing FIG. 1, control unit 100 of PD machine or cycler 20 of system 10 is programmed or configured in one embodiment to use one or more of the patient dwells to remove residual PD fluid from PD fluid containers or bags 38*a* to 38*d*. During a patient dwell a PD cycler is generally typically inactive. Control unit 100 of PD machine or cycler 20 of the present disclosure, on the other hand, makes use of the ample time provided during one or more patient dwell, so that PD fluid containers or bags 38*a* to 38*d* are empty, or as empty as possible, at the end of treatment. In this way, the patient or caregiver may dispose of PD fluid containers or bags 38*a* to 38*d*, which are lighter and cleaner than if the bags contained residual PD fluid. But the patient does not have to wait and can dispose of PD fluid containers or bags 38*a* to 38*d* immediately after the end of treatment.

In one embodiment, control unit 100 waits for the final patient dwell to remove any residual PD fluid from any of PD fluid containers or bags 38*a* to 38*d*. During the final patient dwell, control unit 100 causes appropriate valves, e.g., valves 54*a*, 54*b*, 54*c* and 94*a*, to be opened or toggled at different times to pull residual PD fluid from a desired PD fluid container or bag 38*a* to 38*d*, respectively, via PD fluid pump 70. During each of the different bag draining sequences, control unit 100 also causes valve 54*d* and drain valve 54*i* to be opened so that PD fluid pump 70 may pump residual PD fluid from one of the PD fluid containers or bags 38*a* to 38*d* to drain via drain line 36.

In an alternative embodiment, control unit 100 uses each patient dwell of a treatment, or at least one intermediate patient dwell to remove any residual PD fluid from the most recently used PD fluid container or bag 38*a* to 38*d*. Suppose that the first patient fill is from PD fluid container or bag 38*a*. In one example, during the following patient dwell, control unit 100 causes valves 54*a*, 54*d* and 54*i* to be opened to pump residual PD fluid from PD fluid container or bag 38*a* to drain via PD fluid pump 70. Suppose that the next patient fill is from PD fluid container or bag 38*b*. In one example, during the following patient dwell, control unit 100 causes valves 54*b*, 54*d* and 54*i* to be opened to pump residual PD fluid from PD fluid container or bag 38*b* to drain via PD fluid pump 70. Suppose that the third patient fill is from PD fluid container or bag 38*c*. In one example, during the following patient dwell, control unit 100 causes valves 54*c*, 54*d* and 54*i* to be opened to pump residual PD fluid from PD fluid container or bag 38*c* to drain via PD fluid pump 70.

It is also possible that any one or more PD fluid container or bag 38*a* to 38*d* contains more than one patient fill volume's worth of fresh PD fluid. Control unit 100 knows the volume of each PD fluid container or bag 38*a* to 38*d* in one embodiment and is configured to wait until the patient dwell occurring after the PD fluid container or bag 38*a* to 38*d* has been almost fully emptied before attempting to fully drain any residual PD fluid to drain in a manner described herein. To this end, control unit 100 also knows how much fresh PD fluid has been drained from each of PD fluid container or bag 38*a* to 38*d*. In one embodiment, PD fluid pump 70 is an inherently accurate pump, such as a piston pump, for which each stroke volume is known and accurately pumped. Here, control unit 100 counts the number of pump strokes made by PD fluid pump 70 for each PD fluid container or bag 38*a* to 38*d* and multiplies the number of strokes by the known stroke volume to arrive at the total volume of fresh PD fluid removed from the PD fluid container or bag 38*a* to 38*d*. In another embodiment, PD fluid pump 70 operates with a flowmeter (not illustrated) that outputs to control unit 100. The output of the flowmeter is integrated over the time that PD fluid pump pumps fresh PD fluid from a given PD fluid container or bag 38*a* to 38*d* to know how much PD fluid has been removed from same.

FIG. 1 illustrates that PD fluid container or bag 38*d* holds icodextrin in one embodiment. Icodextrin is formulated to be delivered to the patient at the end of treatment as a last fill. The icodextrin remains inside the patient until the next nightly treatment or until an intermediary PD fluid exchange, such as a midday exchange. The last fill of icodextrin is the last procedure performed by PD machine or cycler 20 for the treatment, so there is no subsequent patient dwell. Here, control unit 100 may be configured to attempt to pump as much icodextrin as possible to the patient during the last fill. Control unit 100 may then cause any residual icodextrin remaining in PD fluid container or bag 38*d* at the end of the last fill to be pumped to drain (e.g., using PD fluid pump 70 with three-way valve 94*a* toggled and valves 54*d* and 54*i* opened). The patient or caregiver may alternatively shut down PD machine or cycler 20 at the end of treatment and transport PD fluid container or bag 38*d* with any residual icodextrin (but all other containers or bags 38*a* to 38*c* empty or virtually empty) for disposal.

Figure 4:
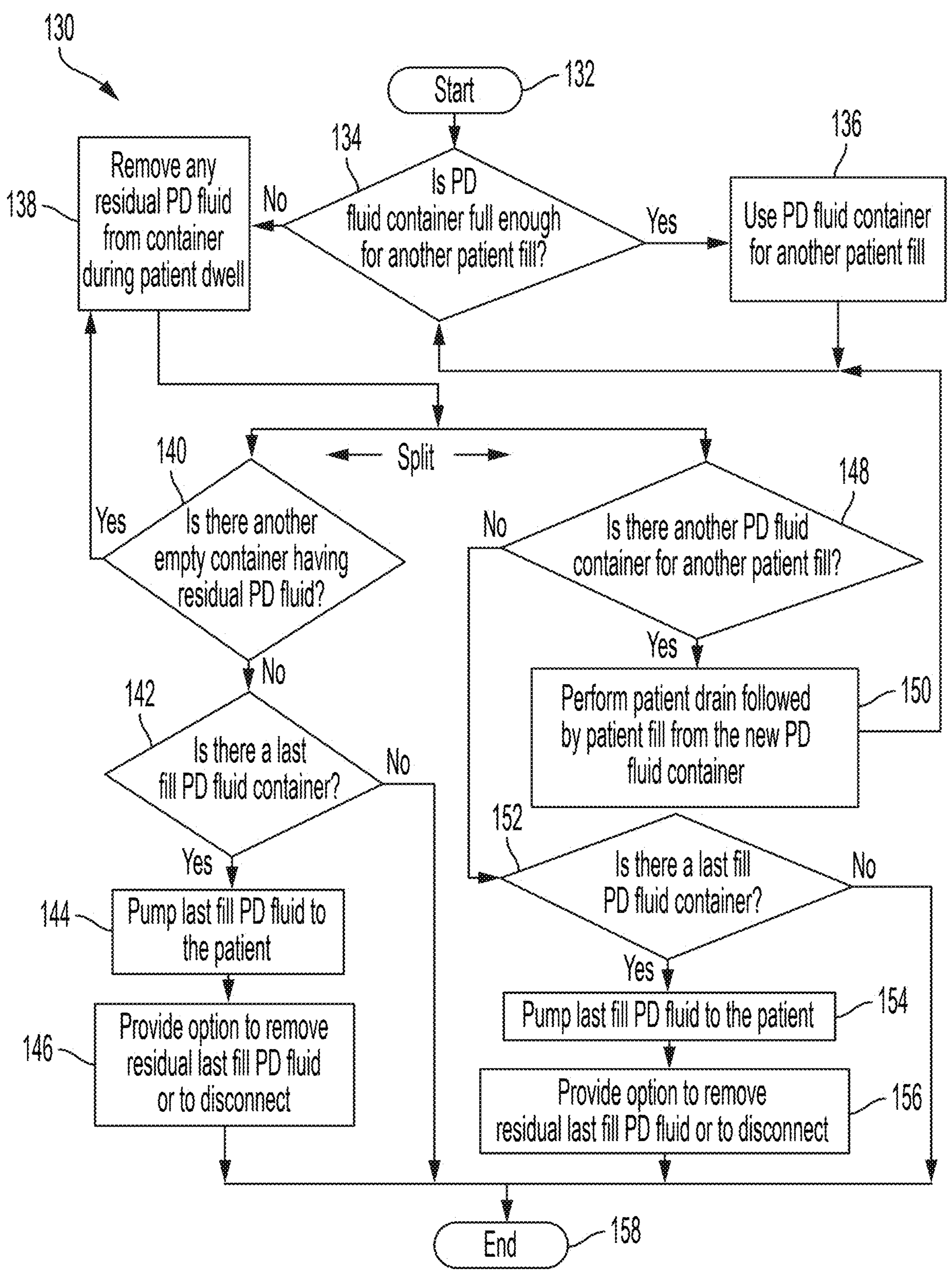
FIG. 4 is a process flow diagram summarizing one embodiment for a peritoneal dialysis container emptying method of the present disclosure.

Method 130 of FIG. 4 summarizes one embodiment for the PD fluid container emptying structure and methodology of system 10 of the present disclosure. At oval 132, method 130 begins. At diamond 134, control unit 100 determines if a previously used PD fluid container or bag 38*a* to 38*d* is too close to being empty to be used for another patient fill. At block 136, if the previously used PD fluid container or bag 38*a* to 38*d* still has enough PD fluid to perform a patient fill, then control unit 100 causes the same PD fluid container or bag to be used to perform the next patient fill and then returns to diamond 134. At block 138, if the previously used PD fluid container or bag 38*a* to 38*d* is close to empty and does not have enough PD fluid to perform a patient fill, then control unit 100 during a subsequent patient dwell causes any residual PD fluid remaining in the PD fluid container or bag 38*a* to 38*d* to be pumped to drain (house drain or drain container), e.g., in a manner described herein.

Method 130 then splits. In the embodiment in which all eligible PD fluid containers or bags 38*a* to 38*d* are emptied during the last patient dwell, control unit at diamond 140 determines if there is another PD fluid container or bag having residual PD fluid to empty. If so, control unit 100 during the same last patient dwell returns to block 138 and causes any residual PD fluid remaining in a different eligible PD fluid container or bag 38*a* to 38*d* to be pumped to drain, e.g., in a manner described herein. When the residual PD fluid from all eligible PD fluid containers or bags 38*a* to 38*d* has been pumped to drain, control unit 100 at diamond 142 next determines if there is a last fill container or bag 38*d*, e.g., holding icodextrin. If there is a last fill container or bag 38*d*, control unit 100 at block 144, and after a final patient drain, pumps last fill PD fluid from last fill container or bag 38*d* to the patient. At block 146, control unit 100 provides the patient or caregiver an option to immediately pump any residual last fill PD fluid to drain or to allow the patient or caregiver to end treatment and discard the disposable set including last fill container or bag 38*d* having residual last fill PD fluid to drain.

In the embodiment in which the PD fluid containers or bags 38*a* to 38*d* are emptied instead during the next patient dwell, control unit 100 at diamond 148 determines if there is another PD fluid container or bag for another patient fill (other than a last patient fill). If so, control unit 100 at block 150 causes at the appropriate time a patient drain followed by a subsequent patient fill from a different PD fluid container or bag 38*a* to 38*d* to be performed. Method 130 then returns to diamond 134, which is repeated for the different PD fluid container or bag. When at diamond 148, control unit 100 determines that there is no other PD fluid container for another patient fill (other than a last patient fill), control unit 100 at diamond 152 next determines if there is a last fill container or bag 38*d*, e.g., holding icodextrin. If there is a last fill container or bag 38*d*, control unit 100 at block 154, and after a final patient drain, pumps last fill PD fluid from last fill container or bag 38*d* to the patient. At block 156, control unit 100 provides the patient or caregiver an option to immediately pump any residual last fill PD fluid to drain or to allow the patient or caregiver to end treatment and discard the disposable set including last fill container or bag 38*d* having residual last fill PD fluid to drain.

At oval 158, the two splits of method 130 merge and method 130 ends.

Patient Connection Before Drain Check

Viewing FIG. 1 in which patient P is connected to dual lumen patient line via filter set 40, the patient during a patient dwell may disconnect from dual lumen patient line 28, e.g., by disconnecting the patient's transfer set from disposable filter set 40. It is contemplated that user interface 108 provide a button or input that allows the patient to inform control unit 100 of PD machine or cycler 20 that the patient is disconnected from the machine. But even if such an input is provided, the patient may forget to press or actuate the input. In an alternative embodiment, such an input is not provided and the patient is relied upon to reconnect to dual lumen patient line 28 prior to the beginning of the next patient drain.

In any of the scenarios discussed above, the patient may not be present and connected to dual lumen patient line 28 when the next patient drain is initiated. If so, and if the patient upon disconnecting from PD machine or cycler 20 connects distal end 28*e* of dual lumen patient line 28 to patient line connector 32, then a negative pressure applied by PD fluid pump 70 during a subsequent patient drain will result in a negative pressure spike or increase as the negative pressure extends to the closed fresh PD fluid side of the fluid lines within PD machine or cycler 20. If the patient upon disconnecting from PD machine or cycler 20 instead leaves dual lumen patient line 28 unattended, then a negative pressure applied by PD fluid pump 70 during a subsequent patient drain will result in air being drawn into the used PD fluid lumen of dual lumen patient line 28.

To prevent either situation above from occurring, it is contemplated that control unit 100 of PD machine or cycler 20 of system 10 cause PD fluid pump 70 to pump a small amount of fresh PD fluid (which may be heated) towards the patient along dual lumen patient line 28. The small amount of fresh PD fluid pumped may be on the order of one to ten, e.g., five milliliters ("ml") and may be pumped down the fresh PD fluid lumen when dual lumen patient line 28 is employed. In an embodiment for pumping a small amount of fresh PD fluid to the fresh PD fluid lumen of dual lumen patient line 28, control unit 100 causes an appropriate supply valve 54*a* to 54*c* or 94*a*, valve 54*d* and valve 54*f* to be opened (or toggled for three-way valve 94*a*) and for PD fluid pump 70 to pump in a normal treatment direction a number of strokes to supply the set small amount of fresh PD fluid. Alternatively or additionally, since the next treatment procedure is a patient drain, and only a small amount of PD fluid is pumped, control unit 100 may cause a small amount of used PD fluid to be pumped to the used PD fluid lumen of dual lumen patient line 28. Here, control unit 100 causes drain valve 54*i* and used PD fluid valve 54*g* to be opened and for PD fluid pump 70 to pump in an opposite to treatment direction a number of strokes to supply the set small amount of used PD fluid.

If the patient is properly connected to disposable filter set 40 and dual lumen patient line 28 when the small amount of fresh/used PD fluid is pushed towards the patient, an output to control unit 100 from one or more pressure sensor, such as any one or more pressure sensor 78*a*, 78*b*1, 78*b*2 and 78*c*, is characteristic of the patient being properly connected. The output may for example be the same as or similar to the output sensed during a patient fill. Upon determining that the output from the one or more pressure sensor is characteristic of the patient being properly connected for treatment, control unit 100 causes the next patient drain to be commenced.

If the patient is not properly connected to disposable filter set 40 and dual lumen patient line 28 when the small amount of fresh/used PD fluid is pushed towards the patient, and wherein distal end 28*e* of dual lumen patient line 28 is parked at and connected to patient line connector 32, an output to control unit 100 from one or more pressure sensor, such as any one or more pressure sensor 78*a*, 78*b*1, 78*b*2 and 78*c*, shows a positive pressure increase that is characteristic of distal end 28*e* of dual lumen patient line 28 being connected to patient line connector 32. Here, the small amount of fresh/used PD fluid added to dual lumen patient line 28 and the internal PD fluid lines of PD machine or cycler 20 will result in a characteristic increase of positive pressure as the additional fluid is pressed into the closed internal lines of the PD machine or cycler. Upon determining that the output from the one or more pressure sensor is characteristic of dual lumen patient line 28 being connected improperly to patient line connector 32, control unit 100 causes user interface 108 to audibly, visually or audiovisually alarm or alert and notify the patient that the patient line needs to be removed from patient line connector 32 and to be connected to disposable filter set 40 (which is connected to the patient's transfer set).

In an embodiment, user interface 108 provides a patient line connection confirm button that the patient presses after reconnecting dual lumen patient line 28 to disposable filter set 40. Once one or more processor 102 of control unit 100 receives the confirm input from user interface 108, the control unit causes the next patient drain to be commenced. If after a certain amount of time, the patient does not press the confirm button at user interface 108, control unit 100 makes a time-out determination, halts treatment and causes user interface 108 to audibly, visually or audiovisually alarm or alert and notify the patient that the current treatment has been stopped.

In an alternative embodiment, the patient line connection confirm button is not provided and instead control unit 100 waits a predetermined amount of time, e.g., one minute, after the audio, visual or audiovisual patient line reconnection alarm or alert. Control unit 100 then causes PD fluid pump 70 to pump another small amount of fresh/used PD fluid (which may be heated) towards the patient along dual lumen patient line 28 and monitors the output from one or more pressure sensor 78*a*, 78*b*1, 78*b*2 or 78*c*. The above process is repeated until a reading from one or more pressure sensor 78*a*, 78*b*1, 78*b*2 or 78*c* is indicative of the patient having reconnected dual lumen patient line 28 to disposable filter set 40. Control unit then causes the next patient drain to be commenced. If after a certain number of attempts, the reading from one or more pressure sensor 78*a*, 78*b*1, 78*b*2 or 78*c* is still indicative of the patient not having reconnected dual lumen patient line 28 to disposable filter set 40, control unit 100 halts treatment and causes user interface 108 to audibly, visually or audiovisually alarm or alert and notify the patient that the current treatment has been stopped.

If the patient is not properly connected to disposable filter set 40 and dual lumen patient line 28 when the small amount of fresh/used PD fluid is pushed towards the patient, and wherein distal end 28*e* of dual lumen patient line 28 has been left unattended and unconnected by the patient, then an output to control unit 100 from one or more pressure sensor, such as any one or more pressure sensor 78*a*, 78*b*1, 78*b*2 and 78*c*, shows a different pressure than if the patient line is connected to the patient.

Upon determining that the output from one or more pressure sensor 78*a*, 78*b*1, 78*b*2 and 78*c* is characteristic of dual lumen patient line 28 being left unattended and unconnected by the patient, control unit 100 causes user interface 108 to audibly, visually or audiovisually alarm or alert and notify the patient that the patient line needs to be connected to disposable filter set 40 (which is connected to the patient's transfer set). User interface 108 may again provide the confirm button for the patient to confirm when dual lumen patient line 28 has been reconnected to disposable filter set 40. Or, control unit 100 as described above may wait a certain amount of time before causing another small amount of fresh/used PD fluid to be delivered to one or both lumens of dual lumen patient line 28. If the confirm button is pressed or a pressure reading from one of the additional PD fluid pushes indicates the patient line being reconnected, control unit 100 causes the next patient drain to be commenced. If instead the confirm button is not pressed after a time-out period, or if a pressure reading after a predetermined number of PD fluid push attempts does not indicate the patient line being reconnected, control unit 100 halts treatment and posts an alarm or alert informing the patient of same as has been described herein.

Figure 5:
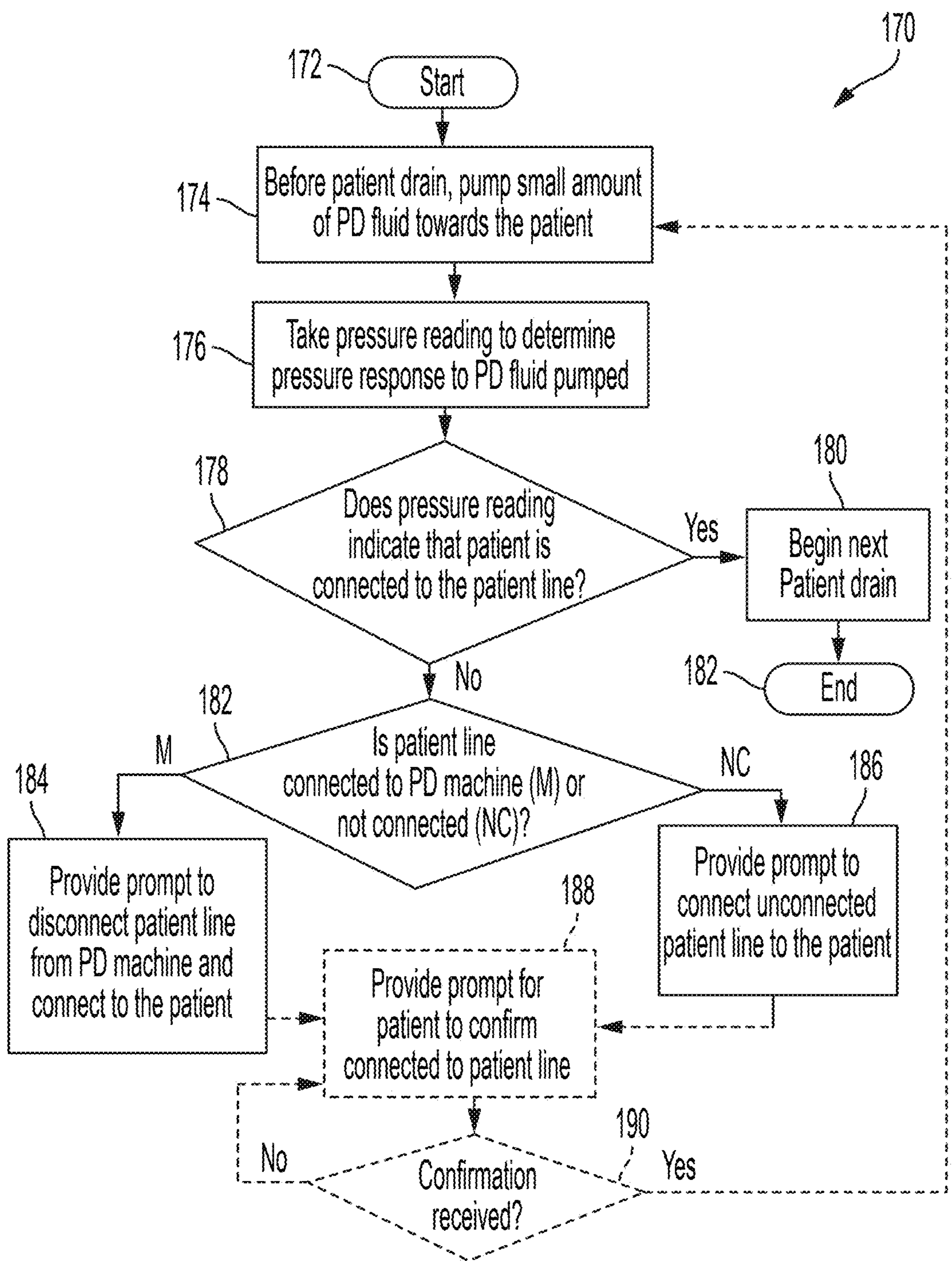
FIG. 5 is a process flow diagram summarizing one embodiment for a patient connection before drain check of the present disclosure.

Method 170 of FIG. 5 summarizes one embodiment for the patient connection before drain check structure and methodology of system 10 of the present disclosure. At oval 172, method 170 begins. At block 174, at the end of a patient dwell and prior to beginning a patient drain, control unit 100 causes a small amount of fresh PD fluid to be pumped into the fresh fluid lumen of dual lumen patient line 28 and/or a small amount of used PD fluid to be pumped into the fresh fluid lumen of dual lumen patient line 28, e.g., in a manner described herein. At block 176, control unit 100 causes one or more reading from one or more relevant pressure sensor to determine the response to the small amount of fluid delivery. At diamond 178, control unit 100 determines if the pressure response to the small amount of fluid delivery indicates that the patient is properly connected to dual lumen patient line 28. At block 180, if the determined pressure response to the small amount of fluid delivery indicates that the patient is properly connected to dual lumen patient line 28, then control unit 100 causes a next patient drain to begin.

At diamond 182, if the determined pressure response to the small amount of fluid delivery indicates that the patient is not properly connected to dual lumen patient line 28, then control unit 100 determines if the pressure response indicates that dual lumen patient line 28 is (i) connected to the PD machine or cycler 20 or (ii) not connected and unattended (dangling). At block 184, if the pressure response indicates that dual lumen patient line 28 is connected to the PD machine or cycler 20, control unit 100 causes user interface 108 to audibly, visually or audiovisually prompt the patient to remove dual lumen patient line 28 from the PD machine or cycler 20 and to connect same to filter set 40 in advance of the next patient drain. At block 186, if the pressure response indicates that dual lumen patient line 28 is not connected and unattended, control unit 100 causes user interface 108 to audibly, visually or audiovisually prompt the patient to retrieve dual lumen patient line 28 and to connect same to filter set 40 in advance of the next patient drain.

Method 170 at block 188 may optionally (shown in phantom) audibly, visually or audiovisually prompt the patient to confirm when the dual lumen patient line 28 is properly connected for the next patient drain. At diamond 190, control unit 100 may optionally (shown in phantom) wait for a confirmation at user interface 108 from the patient that dual lumen patient line 28 is properly connected for the next patient drain. Upon receiving confirmation at diamond 190, or alternatively after a certain period of time after the prompt of block 184 or block 186, method returns to block 174 and pumps another small amount of PD fluid to confirm via a pressure reading that dual lumen patient line 28 is properly connected for the next patient drain.

Method 170 ends at oval 192 after the next patient drain is commenced at block 180.

In a further alternative embodiment, method 170 does not provide the prompts at block 184 or block 186, but instead after a certain amount of time returns to block 174 and pumps another small amount of PD fluid to determine again via a pressure reading that dual lumen patient line 28 is properly connected for the next patient drain.

In still a further alternative embodiment, method 170 after receiving confirmation at diamond 190, relies on the confirmation, does not return to block 174 and instead causes the next patient drain to be commenced.

It should be understood that various changes and modifications to the presently preferred embodiments described herein will be apparent to those skilled in the art. It is therefore intended that such changes and modifications be covered by the appended claims. For example, system 10 for any of the improved treatment features discussed herein does not have to use redundant or durable components, and may instead employ a disposable set having a disposable pumping portion that contacts the corresponding medical fluid. Such disposable cassette may or may not employ disposable filter set 40. For example, while disposable filter set 40 would not be needed as a last chance filter for a system not having heat disinfection, disposable filter set 40 may still be provided if the fresh PD fluid is made online at the time of use as a last chance filter for the online PD fluid. PD fluid pumping with the disposable set may be performed alternatively via pneumatic pump actuation of a sheet of a disposable cassette of the disposable set, via electromechanical pump actuation of a sheet of a disposable cassette of the disposable set, or via peristaltic pump actuation of a pumping tube segment provided with the disposable set. Also, while it is taught to apply negative pressure to reusable dual lumen patient line 28 for spillage prevention, it is contemplated to instead apply negative pressure to a reusable single lumen patient line for spillage prevention.

Additionally, while the container or bag emptying structure and functionality of the present disclosure are described in connection with pumping residual fresh PD fluid to drain, it is contemplated to provide additional fluid lines and valves that allow control unit 100 instead to cause residual PD fluid to be pumped to another PD fluid container or bag. Instances occur during treatment in which fresh PD fluid needs to be discarded and pumped to drain. Examples include overheating or underheating the fresh PD fluid at inline resistive heater 56, wherein instead of pumping the overheated or underheated PD fluid to patient P, the fluid is pumped to drain until properly heated PD fluid is detected. Another example includes the detection of air within the fresh PD fluid. In any case, the pumping of fresh PD fluid to drain may result in a shortage of fresh PD fluid. So here, pumping residual PD fluid from an earlier used PD fluid containers or bags to a later used PD fluid container or bag conserves fresh PD fluid for later if needed, while still emptying the earlier used PD fluid containers or bags. The residual pumping to a later used container or bag may as above occur only during the last patient dwell or may be spread out over two or more patient dwells. During the last patient dwell, control unit 100 causes any residual PD fluid in the later used PD fluid container or bag to be pumped to drain in a manner described above.

Further, while the patient connection before drain check structure and functionality of the present disclosure are described in connection with disposable filter set 40 illustrated in FIG. 1, disposable filter set 40 is not required. Instead, patient line 28, which may be a dual lumen or single lumen patient line, may be connected directly to the patient's transfer set. Still further, while it has been described to pump a small amount of used PD fluid into the used PD fluid lumen of dual lumen patient line 28 for the connection check, the tubing or line configuration of PD machine or cycler 20 may be modified such that a small amount of fresh PD fluid may be pumped instead into the used PD fluid lumen for the connection check.

The invention is claimed as follows:

1. A peritoneal dialysis ("PD") system comprising:

a housing;

a PD fluid pump housed by the housing;

a reusable patient line extending from the housing, the reusable patient line including a distal end configured to be connected to a patient line connector provided by the housing;

at least one reusable PD fluid line extending from the housing, the at least one reusable PD fluid line including a distal end configured to be connected to a PD fluid line connector provided by the housing; and a control unit configured to cause, prior to any of the lines being connected for treatment, the PD fluid pump to apply a negative pressure to at least one of the reusable patient line or the at least one reusable PD fluid line when connected, respectively, to the patient line connector and the PD fluid line connector.

2. The PD system of claim 1, wherein the reusable patient line is a dual lumen patient line including a fresh PD fluid lumen and a used PD fluid lumen, and wherein the negative pressure is applied to at least one of the fresh PD fluid lumen and the used PD fluid lumen.

3. The PD system of claim 2, wherein the negative pressure is applied to the fresh PD fluid lumen by running the PD fluid pump in a reverse to treatment direction, and the negative pressure is applied to the used PD fluid lumen by running the PD fluid pump in the treatment direction.

4. The PD system of claim 1, further comprising a plurality of PD fluid line valves, wherein the negative pressure is applied to the at least one reusable PD fluid line via the PD fluid pump and by sequentially opening the plurality of PD fluid line valves.

5. The PD system of claim 1, wherein the negative pressure is from −5 kPa (−0.73 psig) to −15 kPa (−2.2 psig).

6. The PD system of claim 1, wherein the reusable patient line is connected to the patient line connector and the at least one reusable PD fluid line is connected to at least one PD fluid line connector during a disinfection sequence, and wherein the negative pressure is applied automatically after the disinfection sequence.

7. The PD system of claim 6, wherein the housing houses internal PD fluid lines, the reusable patient line and the at least one reusable PD fluid line forming a closed PD fluid loop with the internal PD fluid lines for the disinfection sequence.

8. The PD system of claim 1, further comprising a user interface, the control unit further configured to cause the user interface to provide a message to wait to remove the reusable patient line and the at least one reusable PD fluid line from the housing until a line disconnection preparation sequence is completed.

9. The PD system of claim 1, further comprising a user interface, the control unit further configured to cause the user interface to provide a message that the reusable patient line and the at least one reusable PD fluid line are ready to be removed from the housing.

10. The PD system of claim 9, wherein the user interface is further configured to provide a moving graphic illustrating a proper way for the distal end of the reusable patient line or the at least one reusable PD fluid line to be removed from the housing.

11. The PD system of claim 1, wherein the negative pressure causes at least one of the reusable patient line or the at least one reusable PD fluid line to collapse prior to removal from the housing and to expand after removal from the housing, which causes PD fluid to be held within at least one of the reusable patient line or the at least one reusable PD fluid line.

12. The PD system of claim 1, further comprising a disposable filter set for connection to the distal end of the reusable patient line when removed from the housing.

13. The PD system of claim 1, further comprising at least one PD fluid container for connection to the distal end of the at least one reusable PD fluid line when removed from the housing.

14. The PD system of claim 1, wherein at least one of the patient line connector or the at least one PD fluid line connector is horizontally disposed relative to the housing.

15. The PD system of claim 1, wherein the control unit is further configured to cause, prior to any of the lines being connected for treatment, at least one valve to lock the negative pressure at the distal end of the reusable patient line.

16. The PD system of claim 1, wherein the control unit is further configured to cause, prior to any of the lines being connected for treatment, at least one valve to lock the negative pressure at the distal end of the at least one PD fluid line.

17. A peritoneal dialysis ("PD") machine comprising:

a housing;

a PD fluid pump housed by the housing;

a reusable patient line extending from the housing, the reusable patient line including a distal end configured to be connected so that the reusable patient line is placed in fluid communication with at least one internal PD fluid line located within the housing;

at least one reusable PD fluid line extending from the housing, the at least one reusable PD fluid line including a distal end configured to be connected so that the at least one PD fluid line is placed in fluid communication with the at least one internal PD fluid line; and a control unit configured to cause, prior to any of the lines being connected for treatment, the PD fluid pump to apply a negative pressure to at least one of the reusable patient line or the at least one reusable PD fluid line when connected for fluid communication with the at least one internal PD fluid line.

18. The PD machine of claim 17, wherein the reusable patient line is placed in fluid communication with at least one internal PD fluid line and the at least one reusable PD fluid line is placed in fluid communication with the at least one internal PD fluid line during a disinfection sequence, and wherein the negative pressure is applied automatically after the disinfection sequence.

19. The PD machine of claim 17, wherein the control unit is further configured to cause, prior to any of the lines being connected for treatment, at least one valve to lock the negative pressure at the distal end of the reusable patient line.

20. The PD machine of claim 17, wherein the control unit is further configured to cause, prior to any of the lines being connected for treatment, at least one valve to lock the negative pressure at the distal end of the at least one PD fluid line.

* * * * *